(12) United States Patent
Kanai

(10) Patent No.: US 6,312,411 B1
(45) Date of Patent: Nov. 6, 2001

(54) FLUID SUPPLYING APPARATUS

(75) Inventor: Masahiro Kanai, Tokyo (JP)

(73) Assignee: Aubex Corporation, Tokyo (JP)

( * ) Notice: Subject to any disclaimer, the term of this patent is extended or adjusted under 35 U.S.C. 154(b) by 0 days.

(21) Appl. No.: 09/425,169

(22) Filed: Oct. 22, 1999

(30) Foreign Application Priority Data

Oct. 23, 1998 (JP) .................................................. 10-302381

(51) Int. Cl.$^7$ .................................................. A61M 1/00
(52) U.S. Cl. .......................... 604/153; 604/132; 604/185; 417/472; 417/557; 222/372
(58) Field of Search .................................... 604/131, 132, 604/153, 151, 152, 246, 183, 185, 186, 247, 256, 523, 236, 237, 31, 150, 123, 133, 891.1, 238, 257, 214, 43, 142; 222/372, 633, 95, 206, 328; 128/DIG. 12; 251/342; 417/472, 503, 557

(56) References Cited

U.S. PATENT DOCUMENTS

| 3,330,282 | | 7/1967 | Visser et al. . | |
|---|---|---|---|---|
| 3,429,313 | * | 2/1969 | Romanelli | 128/276 |
| 3,983,872 | * | 10/1976 | Nehring | 128/278 |
| 4,022,209 | * | 5/1977 | Nehring | 128/278 |
| 5,011,477 | * | 4/1991 | Winchell et al. | 604/132 |
| 5,061,253 | | 10/1991 | Yoshida . | |
| 5,224,934 | | 7/1993 | Payne et al. . | |
| 5,360,411 | * | 11/1994 | Mimura et al. | 604/246 |
| 5,503,628 | | 4/1996 | Fetters et al. . | |
| 5,746,714 | | 5/1998 | Salo et al. . | |
| 5,782,802 | | 7/1998 | Landau . | |
| 5,891,102 | * | 4/1999 | Hiejima et al. | 604/185 |
| 5,938,637 | | 8/1999 | Austin et al. . | |
| 6,017,318 | * | 1/2000 | Gauthier et al. | 600/578 |
| 6,024,724 | * | 2/2000 | Lee | 604/132 |
| 6,027,491 | * | 2/2000 | Hiejima et al. | 604/891.1 |
| 6,213,981 | * | 4/2001 | Hiejima et al. | 604/185 |

FOREIGN PATENT DOCUMENTS

| 0 483 759 | 5/1992 | (EP) . |
|---|---|---|
| 0 885 620 | 12/1998 | (EP) . |
| 51-21927 | 2/1976 | (JP) . |
| 3-505538 | 12/1991 | (JP) . |
| WO90/12609 | 11/1990 | (WO) . |

* cited by examiner

Primary Examiner—Richard K. Seidel
Assistant Examiner—Cris L. Rodriguez
(74) Attorney, Agent, or Firm—Lowe Hauptman Gilman & Berner, LLP

(57) ABSTRACT

A fluid supplying apparatus having a rubber elastic film (11) with fluid contained therein, an upstream tube (30), an intermediate station (40) disposed at a distal end of the upstream tube (30) and a downstream tube (27) connected to the intermediate station (40) is provided. The upstream tube (30) has two flow paths (31A and 32A) formed in a predetermined length extending in a longitudinal direction. The intermediate station (40) has a case (41), the case (41) having a fluid outlet (51) to which the downstream tube (27) is connected, a first communicating channel (52) for intercommunicating the fluid outlet (51) and one of the flow paths (31A), a reservoir (53) in communication with the other flow path (32A), a second communicating channel (55) having a check valve (54) at an intermediate portion thereof and intercommunicating the reservoir (53) and the fluid outlet (51), and a pressing member (56) for discharging the fluid stored in the reservoir (53) to the second communicating channel (55).

6 Claims, 8 Drawing Sheets

FLUID SUPPLYING APPARATUS

BACKGROUND OF THE INVENTION

1. Field of the Invention

The present invention relates to a fluid supplying apparatus for continuously and gradually supplying fluid contained within a fluid container and for supplying a predetermined fluid at a stroke as necessary.

More specifically, it relates to a fluid supplying apparatus for continuously supplying medical fluid, transfusion and so on to a living body such as a human body and an animal, for continuously and as necessary supplying plants with water, nutrients (fluid), medical fluid (an insecticide fluid) and so on, and for continuously and as necessary supplying a fish aquarium with medical fluid such as an antibiotic, bait (fluid), nutrients (fluid) for water plants and so on.

2. Description of Related Art

Small quantity of medical fluid such as analgesic drug is continuously given to a patient after operation for alleviating headache and so on in hospitals.

Further, some patients feel pains even when the medical fluid such as analgesic drug is continuously given at a small quantity. In this case, additional predetermined amount of analgesic drug is prescribed by doctors to the patients each time the patient feel the pain.

However, doctors or nurses have to undergo injection or the like for such additional prescription of the medical fluid. Therefore, such treatment can be burden for the doctors and nurses and patients feel pain and anxiety during the treatment.

Accordingly, an apparatus for giving the patients a predetermined amount of medical drug by the patients themselves at one time has been desired in addition to continuous injection of the medical fluid.

An apparatus shown in, for example, published Japanese translations of PCT international publication for patent applications No. Hei 3-505538 is known for such request.

The apparatus has a fluid container containing medical fluid and one flexible capillary connected to the fluid container. Two branch tubes are connected to a distal end of the flexible capillary. A syringe for pushing out a predetermined amount of medical fluid as necessary by handling of the patients is connected to one of the branch tubes, where an outlet tube connected to a medical fluid outlet and the other branch tube are collectively connected to one catheter.

In use, the fluid container is accommodated in a breast pocket of the patient and the catheter is inserted to human body (patient) while the injector is wound around wrist by a band or the like.

Ordinarily, the medical fluid contained in the medical fluid container is continuously injected into the human body little by little through the flexible capillary, the other branch tube and catheter.

When the patient feels pain, the patient himself pushes out the medical fluid reserved in the injector to let the predetermined amount of the medical fluid injected to the patient at a stroke through the medical fluid outlet, the outlet tube and catheter, thereby alleviating the pain.

However, in the conventional arrangement, three tubes cross with each other around the injector when the injector is wound around the wrist in use.

In other words, since the two branch tubes and the outlet tube from the injector cross with each other, it is troublesome for the patient to carry and handle it and pushing operation can be hindered.

SUMMARY OF THE INVENTION

An object of the present invention is to provide a fluid supplying apparatus for solving the above disadvantage of the conventional apparatus where no trouble for carrying is caused and superior usability can be obtained.

To attain the above object, a fluid supplying apparatus according to the present invention includes a fluid container for containing fluid; an upstream tube of which base end is connected to the fluid container for leading the fluid contained in the fluid container; an intermediate station provided at a distal end of the upstream tube; and a downstream tube connected to the intermediate station for introducing the fluid going through the intermediate station. The upstream tube is formed in a predetermined length and having therein at least two flow paths along a longitudinal direction thereof. The intermediate station includes a case provided at the distal end of the upstream tube, the case having a fluid outlet to which the downstream tube is connected, a first communicating channel for intercommunicating the fluid outlet and one of the flow paths of the upstream tube, a reservoir in communication with the other flow path of the upstream tube for storing the fluid introduced through the other flow path, a second communicating channel for intercommunicating the reservoir and the fluid outlet and having a check valve at an intermediate portion thereof, and a discharging means for pushing out the fluid stored in the reservoir to the second communicating channel.

In the present invention, the fluid contained in the fluid container is discharged to the outside from the upstream tube through the first communicating channel of the intermediate station and downstream tube. In this condition, namely, continuous discharge condition, when the fluid stored in the reservoir is pushed out to the second communicating channel by a discharging means, the fluid is discharged from the check valve in the second communicating channel through the downstream tube. In other words, a predetermined amount of fluid can be discharged at a stroke as necessary, while the fluid stored in the reservoir is continuously discharged.

At this time, since only two tubes, i.e. the upstream tube and the downstream tube, are disposed around the intermediate station, no trouble is caused in carrying and superior usability can be obtained.

In the present invention, the two flow paths may have a flow control valve at an intermediate portion thereof and are preferably made of thermoplastic tube elements of a predetermined length having deformed opening cross section.

When the opening cross section is not circular but is deformed, since the deformed hole having the same cross sectional area as a circular hole can have larger edge length forming the hole, in other words, can have larger inner circumference length, precise flow control is possible.

In the present invention, though the connecting direction of the upstream tube and the downstream tube to the intermediate station may be determined according to usage, when the medical fluid to be injected to the human body is contained in the fluid container, the upstream tube and the downstream tube may preferably connected to the same side of the intermediate station.

Accordingly, when the fluid container is accommodated in the breast pocket of the patient and the intermediate station is attached to the wrist by bands and the like, since the upstream tube runs along the arm from the breast pocket to the wrist and the downstream tube runs parallel to the upstream tube, the distal end of the downstream tube can be easily inserted to the arm of the patient. In other words, the distal end of the downstream tube can be inserted to the patient while the respective tubes run approximately along the arm without largely bending or twisting the tubes.

In the present invention, the reservoir is preferably made of a balloon for expanding and contracting in accordance with fill and discharge of the fluid, and the discharging means is preferably made of a pressing member insertable into the case for pressing the balloon when being pressed and returnable to original position thereof for returning to the original position in accordance with fill of the fluid into the balloon.

Accordingly, when the pressing member is pushed into the case, the balloon is contracted to discharge the fluid thereinside. When the fluid is filled in the balloon while releasing the press by the pressing member, the pressing member returns to original position, thereby conducting discharge of the fluid from the balloon and fill of the fluid into the balloon with a simple arrangement.

In the above arrangement, a guide wall to be flat with an upper face of the pressing member when the pressing member returns to the original position is preferably provided to at least a part of the surrounding of the case encircling the pressing member, thereby checking that the fluid is filled in the balloon. In other words, one can confirm whether the fluid is filled in the balloon by touching the guide wall by a finger or the like to see the upper faces of the guide wall and the pressing member are approximately flat. Such arrangement, i.e. checking by finger touch, is advantageous for use in darkness such as night.

In the present invention, when the fluid is discharged into the intermediate station from the at least two flow paths of the upstream tube, volume of the first communicating channel is preferably defined so that time for the fluid from one flow path to reach the fluid outlet is longer than time for the fluid from the other flow path reaches the check valve.

Accordingly, when the fluid is initially discharged from the two flow paths of the upstream tube to the intermediate station and the fluid from one of the flow paths is discharged from the fluid outlet, since the fluid from the other flow path reaches the check valve, in other words, the reservoir and the second communicating channel is filled with fluid to eliminate air, initial air removal can be efficiently conducted.

DETAILED DESCRIPTION OF PREFERRED EMBODIMENT(S)

A preferred embodiment of the present invention will be described below with reference to drawings.

Figure 1:
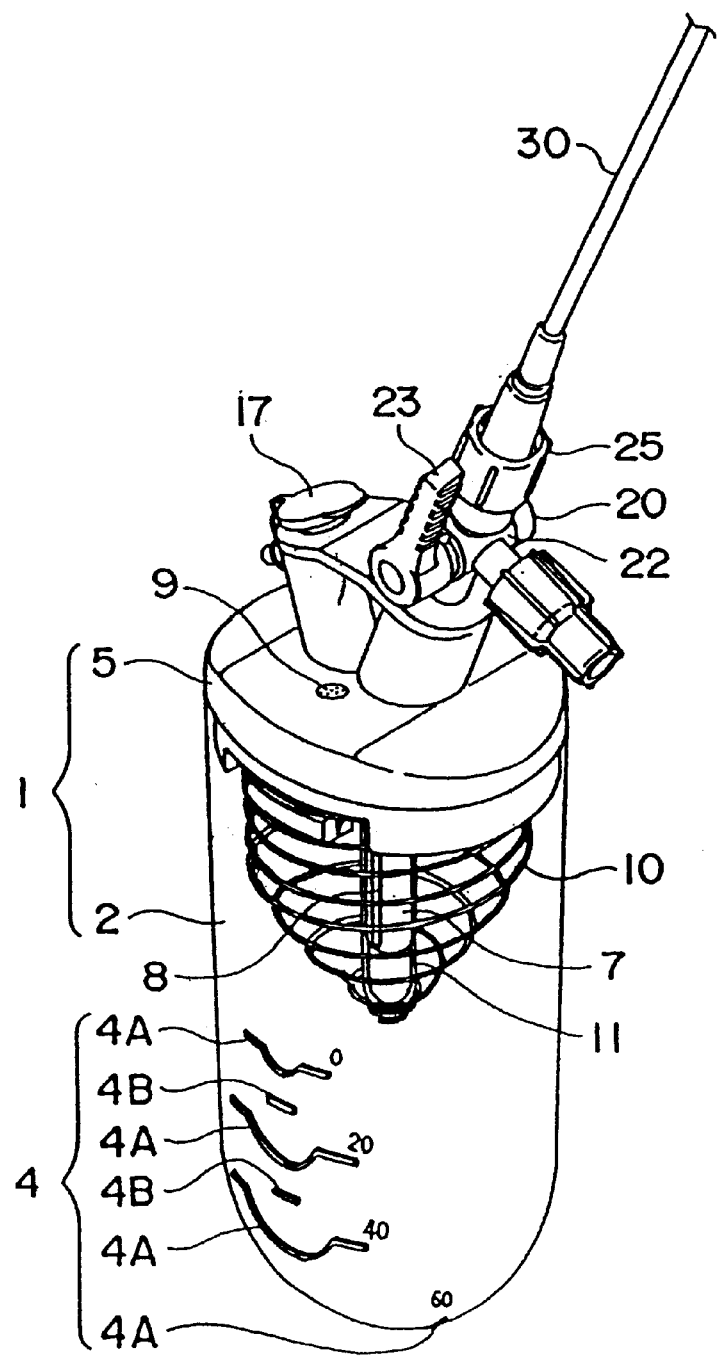
FIG. 1 is a perspective view showing a preferred embodiment of a fluid supplying apparatus according to the present invention.
Figure 2:
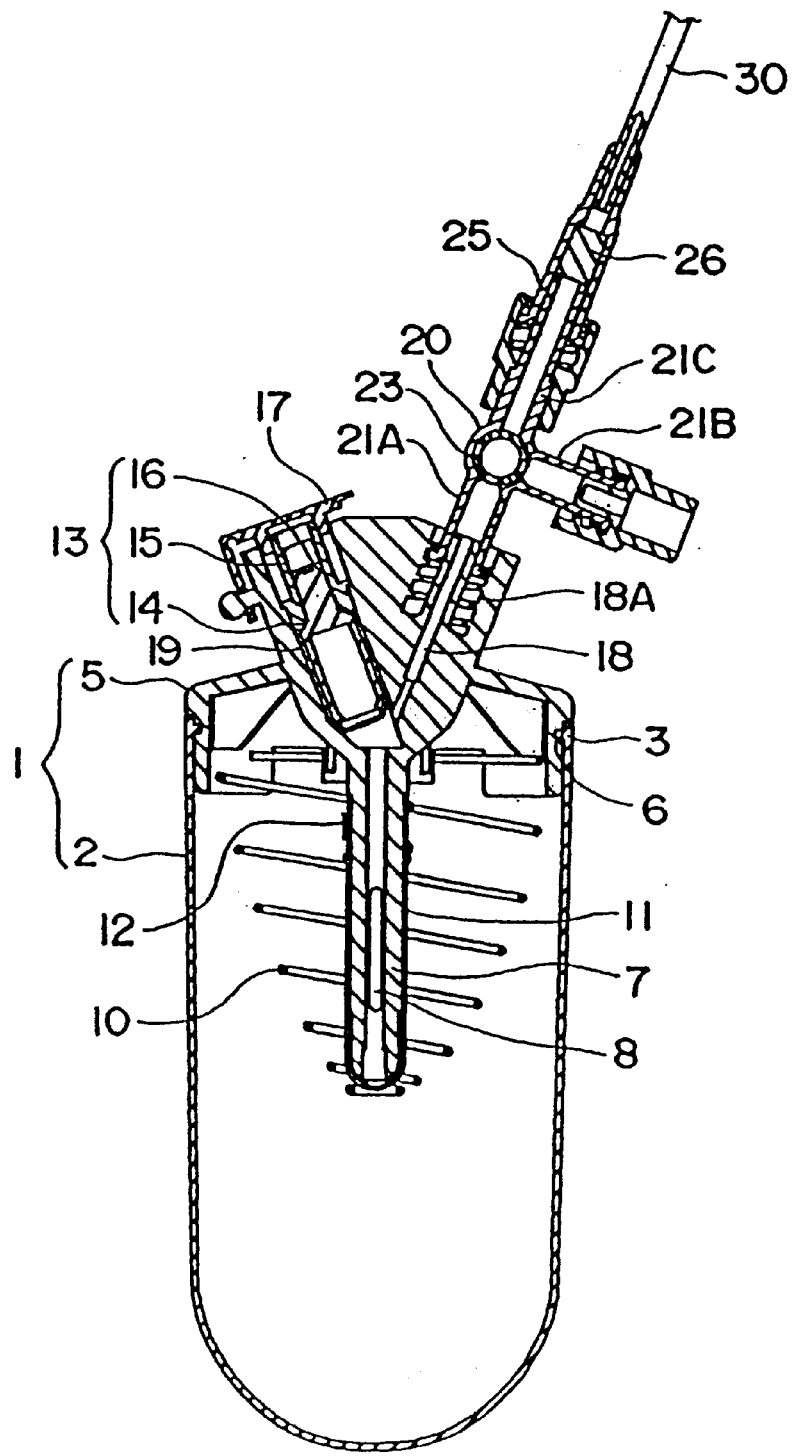
FIG. 2 is a cross-section of the aforesaid embodiment.

In the present embodiment, the present invention is applied to a medical fluid injection apparatus for injecting medical fluid to human body. FIG. 1 is a perspective view thereof, and FIG. 2 is a cross-sectional view thereof. In the figures, reference numeral 1 indicates a protection case which includes a bottomed cylindrical body 2 of transparent material such as plastic and glass, a lid body 5 made of polypropylene and fitted to an open end of the cylindrical body 2.

Figure 3:
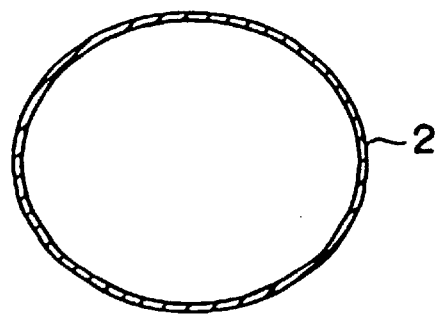
FIG. 3 is a cross-section of a protection case of the aforesaid embodiment.

The cylindrical body 2 is formed in a bottomed cylinder having an inner configuration of deformed cross-section except for circle, an oval here (see FIG. 3), and is provided with a projection 3 on inner side adjacent to the open end and a scale 4 on outer side, respectively. The scale 4 indicates medical fluid containing amount (medical fluid containing amount inside below-mentioned rubber elastic film 11) by cc unit from intermediate position in the up and down direction toward bottom. The scale 4 is composed of even number scale 4A of "0", "20", "40" and "60" and odd number scale 4B of "10", "30" and "50".

Figure 4:
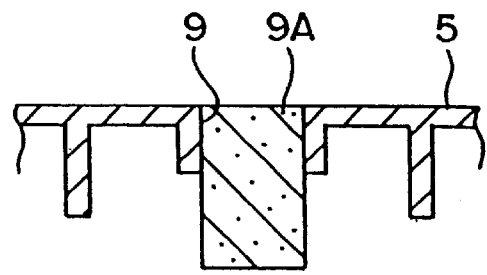
FIG. 4 is a cross-section of a water-repellant breathable filter of the aforesaid embodiment.

The lid body 5 has an engaging concave portion 6 for engaging the projection 3 of the cylindrical body 2 at an outer side thereof, an air vent 9 and a medical fluid introduction tube 7 as a thin fluid introduction tube extending toward inside of the cylindrical body 2 substantially at the center of an upper side thereof. Both ends of the medical fluid introduction tube 7 are opened and a plurality of slits 8 is provided on circumference thereof as shown in FIG. 4. The air vent 9 has a water-repellant breathable filter 9A for circulating air inside and outside of the protection case 1 and preventing the medical fluid from permeating. A chemical-resistant synthetic resin bundle with water-repellant processing is preferably used as the water-repellant breathable filter 9A, for instance.

A rubber elastic film 11 as a fluid container with bottomed-tube shape is fitted in close contact with the medical fluid introduction tube 7, an open end of the rubber elastic film 11 being held by a pinch 12. An outer diameter and length of the medical fluid introduction tube 7 is substantially the same as an inner diameter and length of the contracted rubber elastic film 11. A maximum of 60 cc medical fluid can be contained in the rubber elastic film 11. Incidentally, ordinarily approximate 20 cc medical fluid is injected for cancer pain treating per one day, so that medical fluid for approximately three days can be contained therein.

The rubber elastic film 11 is expanded in accordance with injecting and receiving the medical fluid. A spring 10 stretching in proportion to the expansion of the rubber elastic film 11 is disposed at outer side thereof. The spring 10 is made of wire material having diameter of 0.6 mm to 0.8 mm, for instance. The spring 10 has an upper end stopped to the lid body 5 and is wound in a spiral manner so that the diameter thereof is gradually narrowed downward. The lowermost end is abutted to a pointed end of the medical fluid introduction tube 7 through the rubber elastic film 11.

The rubber elastic film 11 is preferably made of a chemical-resistant material undamaged by a function of medical fluid and having great toughness and stretchability, and transparent or translucent material is especially preferable. For example, silicone rubber and latex rubber on the market are preferable. The thickness of the rubber elastic film is approximately 0.4 mm. A contraction power when the medical fluid is introduced in the rubber elastic film 11 is preferably 1000 to 700 mmAq (millimeter by water head) pressure. Since venous pressure of human body is ordinarily around 60 mmAq, the medical fluid can be introduced to a patient by a pressure more than 60 mmAq. When the contraction power of the rubber elastic film 11 falls below 1000 mmAq, it is difficult to be controlled. When the contraction power exceeds 7000 mmAq, the medical fluid is difficult to be injected from the syringe into the rubber elastic film 11 by human power. However, the contraction power is not limited to the range described above.

An inflow hole 19 as a fluid inflow hole for injecting the medical fluid into the rubber elastic film 11 and an outflow hole 18 as fluid outflow hole for discharging the medical fluid received inside the rubber elastic film 11 are provided adjacently in V-shape on an upper portion of the medical fluid introduction tube 7 (lid body 5). In other words, the inflow hole 19, the outflow hole 18 and the medical fluid introduction tube 7 are provided to the lid body 5 in substantially Y-shaped arrangement and mutually in communication. A check valve 13 for allowing the inflow to the medical fluid introduction tube 7 from the outside and preventing the outflow from the medical fluid introduction tube 7 toward outside is provided inside the inflow hole 19. The check valve 13 has a valve cylinder 15 buried in the inflow hole 19 and having a valve seat 14 at the halfway thereof, and a chemical-resistant valve bar 16 made of silicone rubber and the like and retractably accommodated in the valve cylinder 15 to open and close the valve seat 14. Incidentally, a cap 17 can be releasably attached to an outer end of the valve cylinder 15. A spiral groove 18A for releasably engaging a three-direction valve 20 is formed around the outflow hole 18. The three-direction valve 20 has a valve body 22 with three switch holes 21A, 21B and 21C, and a cock 23 for switching the flow path.

A connector 25 provided on one end of an upstream tube 30 having conduit function and flow rate control function is releasably connected to the switching hole 21C of the three-direction valve 20. A filter 26 for removing dust etc. in the medical fluid is accommodated inside the connector 25.

Figure 5:
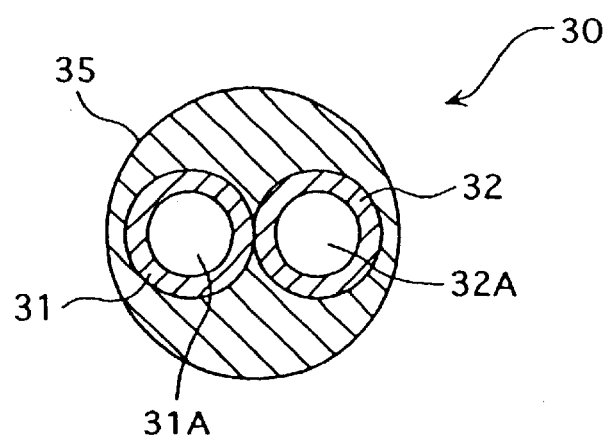
FIG. 5 is a cross-sectional view showing a cross-section of a tube of the apparatus of the aforesaid embodiment.

The tube used for the upstream tube 30 is formed in a predetermined length and has thereinside a plurality of flow paths extending parallel along a longitudinal direction thereof. Specifically, as shown in FIG. 5, the tube includes a plurality of (two) thermoplastic-resin made tube elements 31 and 32 respectively having flow paths 31A and 32A of the same fluid passage rate. The tube elements 31 and 32 are bundled and outer surface thereof is unitedly covered with a covering member 35.

Respective tube elements 31 and 32 may be a single-layered tube, or alternatively, a covered tube considering reinforcement and handling. All of Polypropylene (PP), polyethylene (PE), polyacetals (POM), polycarbonate (PC), ABS, polyamide resin, and polystyrene (PS) can be used for a material of the tube element 31 and 32, however, transparent material is preferable. A flexible material is preferable for the covering member as a cover such as thermoplastic resin elastomer, polyolefin (LDPE, LLDEP) type elastomer, thermoplastic polyurethane elastomer, soft vinyl chloride resin and EVA.

The configuration of the cross-section of the tube element 31 and 32 is deformed unlike a circular opening of conventional flow rate control means. Some examples are shown in FIG. 6.

Figure 6A:
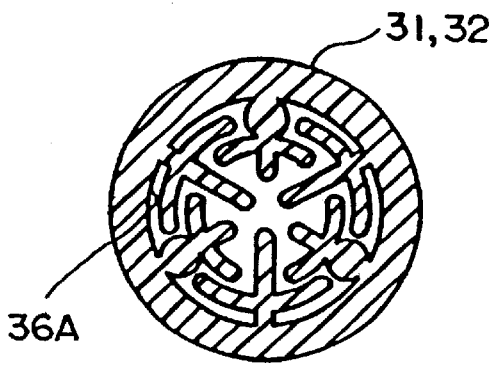
FIGS. 6(A) to 6(E) are cross-sectional views showing different configurations of cross-sections of tube elements of the apparatus of the aforesaid embodiment.

An opening 36A of the tube elements 31 and 32 shown in FIG. 6(A) has three branch-shaped projections of different two types alternatively projecting from an inner circumference of a circular base hole toward the center thereof.

Figure 6B:
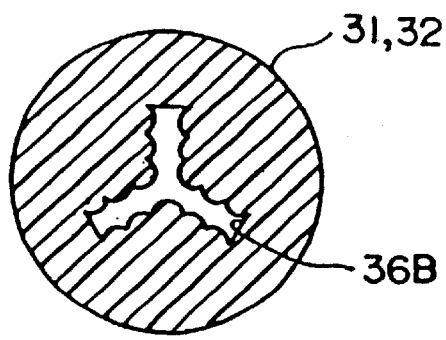

An opening 36B of the tube elements 31 and 32 shown in FIG. 6(B) has approximate rectangular-shaped groove extending in radial direction from the center of the tube elements 31 and 32 located by an even disposition of 120 degrees forming an approximate Y-shaped configuration, the groove having an inner side with concave and convex portion.

Figure 6C:
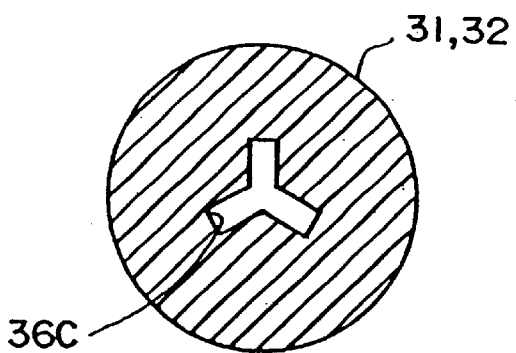

An opening 36C of the tube elements 31 and 32 shown in FIG. 6(C) has no concave and convex portion on the inner side unlike the opening 36B shown in FIG. 6(B) and the radial length of respective rectangular shape is shortened.

Figure 6D:
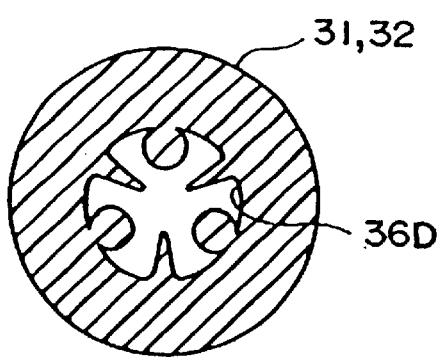
Figure 6E:
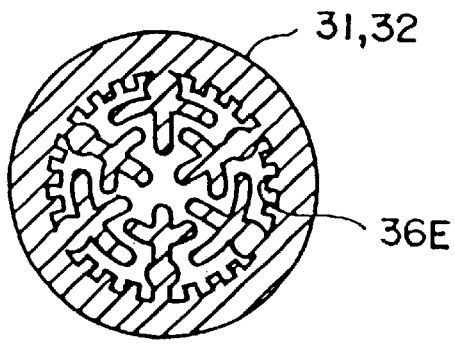

An opening 36D of the tube elements 31 and 32 shown in FIG. 6(D) has three thin triangle and circular projections alternatively projecting from an inner circumference of a circular base hole toward the center thereof An opening 36E of the tube elements 31 and 32 shown in FIG. 6(E) has branch-shaped projections with slightly deformed configuration of FIG. 6(A) and internal-gear-shaped concave and convex portion inside the base hole.

The deformation effect of deformed opening of the tube elements 31 and 32 is prominent when the deformation degree represented by square root of inner circumferential dimension of opening/opening cross-sectional area exceeds 7, and the above respective opening 36A to 36E have great deformation degree exceeding 7.

Incidentally, the above-described tube elements 31 and 32 having minute and deformed opening configuration can be molded using a die shown in Japanese Patent Application Laid-Open No. Sho 51-21927. In the molding method, a die for monofilament having a multiple of resin introduction hole provided to an area substantially the same as the outer diameter of the tube elements 31 and 32 and having no hole to a portion corresponding to the opening 36A to 36E is used. A molten resin monofilament is extruded from the introduction holes and the multiple of close monofilament is fused to obtain the tube elements 31 and 32 with minute and deformed configuration. However, the manufacturing method of the tube elements 31 and 32 is not limited to the method.

Figure 7:
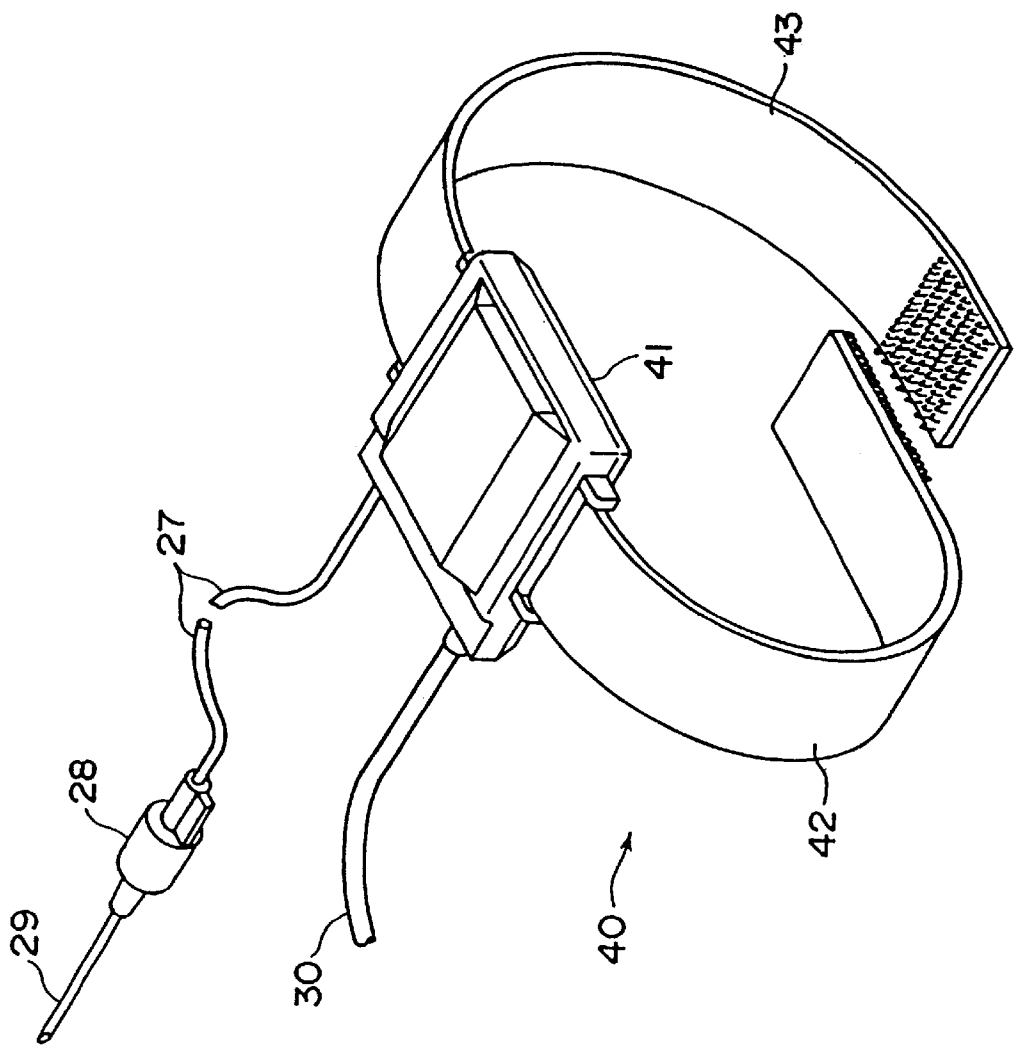
FIG. 7 is a perspective view showing an intermediate station used in the aforesaid embodiment.

An intermediate station 40 is connected to the other end of the upstream tube 30 as shown in FIG. 7. A connector 28 similar to the connector 25 is fixed to the intermediate station 40 through a downstream tube 27 having a single flow path thereinside. A syringe needle 29 as an attachment to human body is releasably attached to a distal end of the connector 28. Accordingly, an inside of the rubber elastic film 11 and the syringe needle 29 as the attachment to human body are connected through the upstream tube 30, the intermediate station 40 and the downstream tube 27.

The intermediate station 40 has a flat rectangular case 41 provided at the distal end of the upstream tube 30. The case 41 is formed by a material such as polyethylene (PE), polycarbonate (PC) and polypropylene (PP) and can be attached to wrist etc. by a pair of engageable band 42 and 43 by a single touch.

Figure 8:
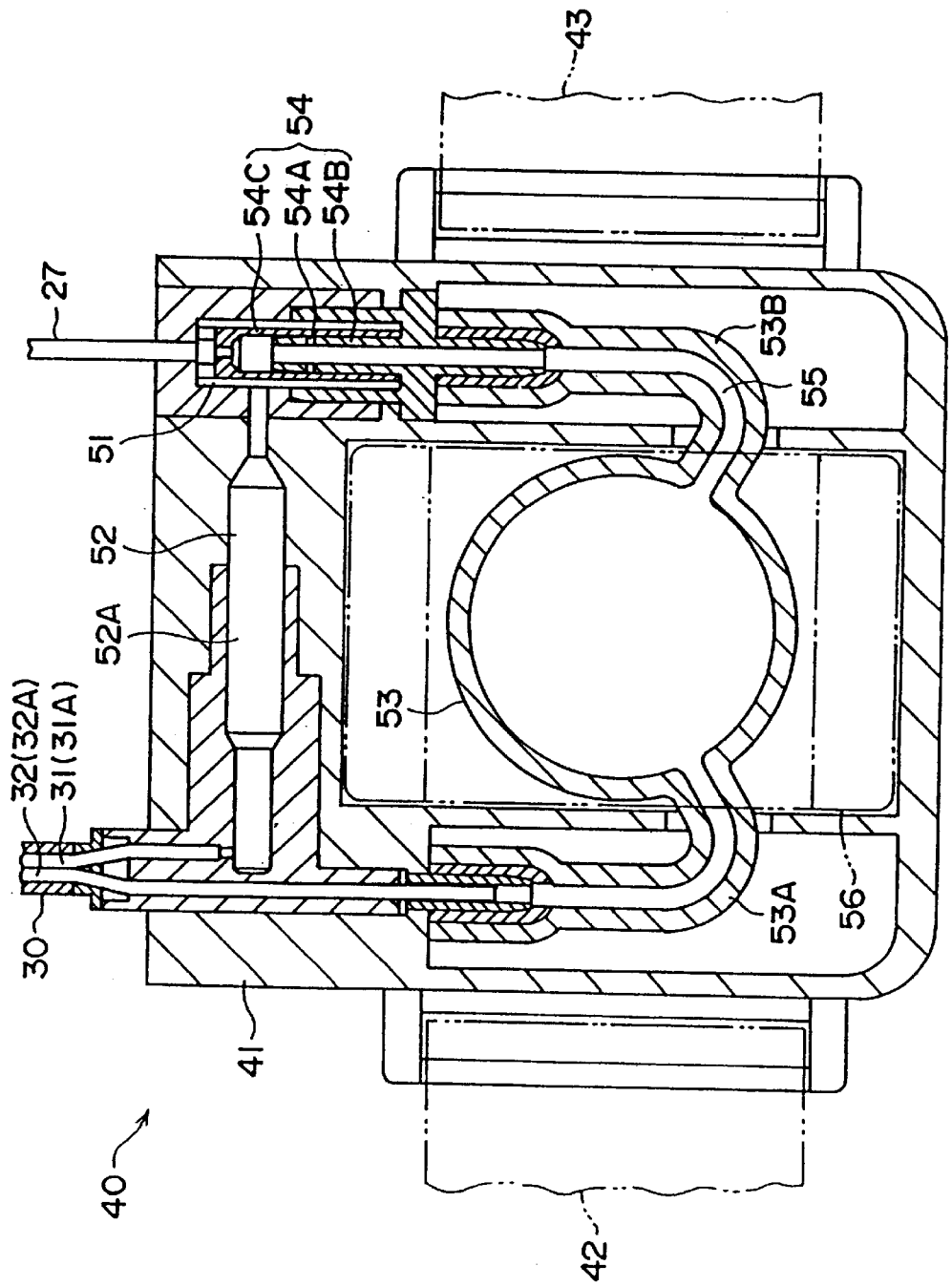
FIG. 8 is a cross section showing the intermediate station used in the aforesaid embodiment.
Figure 9:
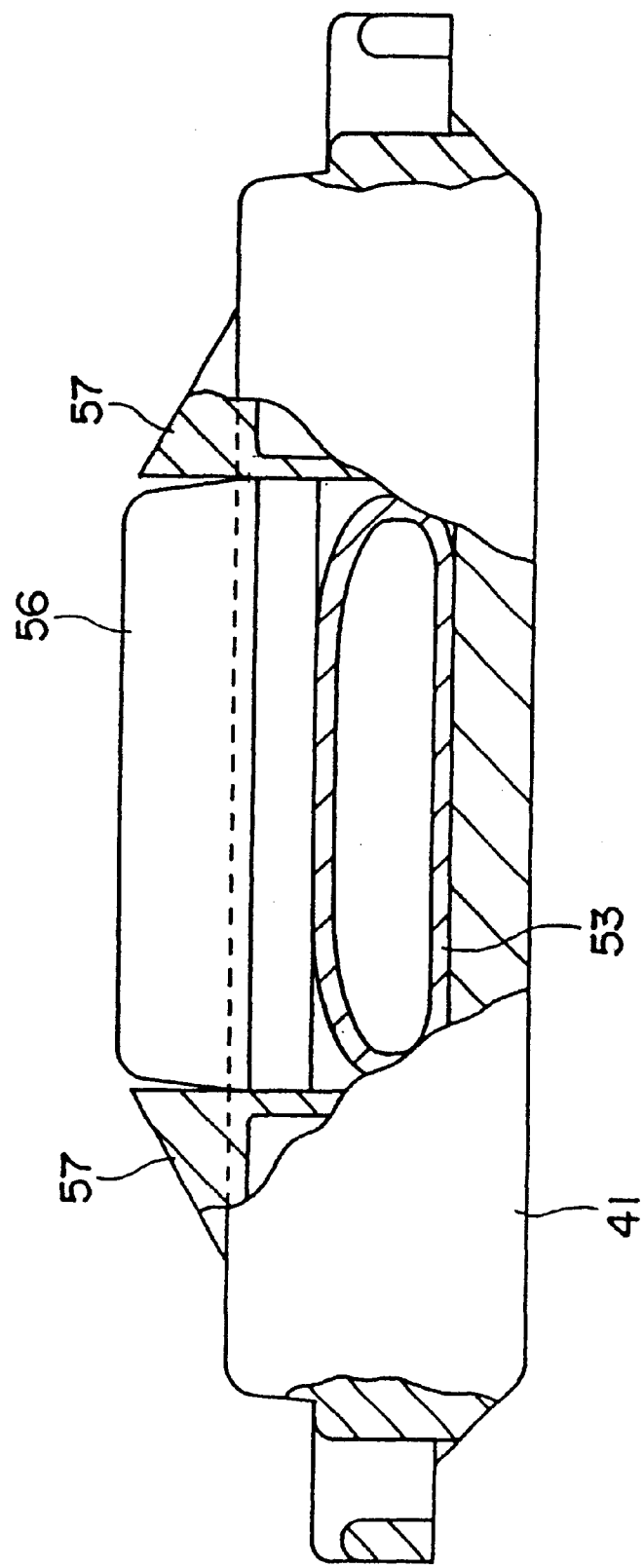
FIG. 9 is a side elevation showing the intermediate station used in the aforesaid embodiment.

As shown in FIGS. 8 and 9, the case 41 has a fluid outlet 51 for the downstream tube 27 to be connected, first communicating channel 52 for intercommunicating the fluid outlet 51 and the flow path 31A within one of the tube elements 31 of the upstream tube 30, a reservoir 53 communicating to the flow path 32A within the other tube element 32 of the upstream tube 30 for storing the medical fluid introduced through the flow path 32A, second communicating channel 55 for intercommunicating the reservoir 53 and the fluid outlet 51 and having a check valve 54 at an intermediate portion thereof, and a pushing member 56 as a discharging means for pushing out the medical fluid stored in the reservoir 53 to the second communicating channel 55.

The fluid outlet 51 is formed on a side of the case 41 to which the upstream tube 30 is connected. Accordingly, the upstream tube 30 and the downstream tube 27 are connected to the same side of the case 41 of the intermediate station 40.

A fluid receiving portion 52A is formed at an intermediary of the first communicating channel 52, which is provided for controlling the volume of the first communicating channel 52 so that the time for the medical fluid from the flow path 31A to reach the fluid outlet 51 is longer than the time for the medical fluid from the flow path 32A to reach the check valve 54 when the medical fluid is discharged from the two flow paths 31A and 32A to the intermediate station 40.

The reservoir 53 is made of an elastic balloon for expanding and contracting by filling and discharging the medical fluid. The balloon is preferably made of a chemical-resistant material undamaged by a function of medical fluid and having great toughness and stretchability. For example, superposed two resin sheets such as polyvinyl chloride, polyethylene and polypropylene configured into a bag-shape by bonding periphery thereof can be suitably used. Incidentally, the connecting portion derived out of the circular fluid container (connecting portion 53A to the upstream tube 30 and connecting portion 53B structuring the second communicating channel 55) is made of a non-expandable and non-contractible material.

The check valve 54 includes a nozzle 54B attached to a distal end of the connecting portion 53B structuring the second communicating channel 55 and having a hole 54A around a distal portion thereof, and an elastic cylindrical tube 54C fitted to outer circumference of the nozzle 54B. Accordingly, when the medical fluid stored in the balloon (the reservoir 53) is pushed out into the second communicating channel 55 by being pushed out by the pressing member 56, the medical fluid is discharged to the fluid outlet 51 from the hole 54A of the nozzle 54B through a space between outer circumference of the nozzle 54B and the tube 54C while preventing the medical fluid from back-flow from the fluid outlet 51 to the second communicating channel 55.

The pressing member 56 is provided in the case 41 insertably and returnably to original position to press the balloon (the reservoir 53) during insert and to return to the original position in accordance with filling the medical fluid in the balloon (the reservoir 53). At this time, an upper face of a triangular guide wall provided on both sides of the surrounding of the case 41 encircling the pressing member 56 is made flat with an upper face of the pressing member 56.

A using method of the present embodiment will be described below.

Figure 10:
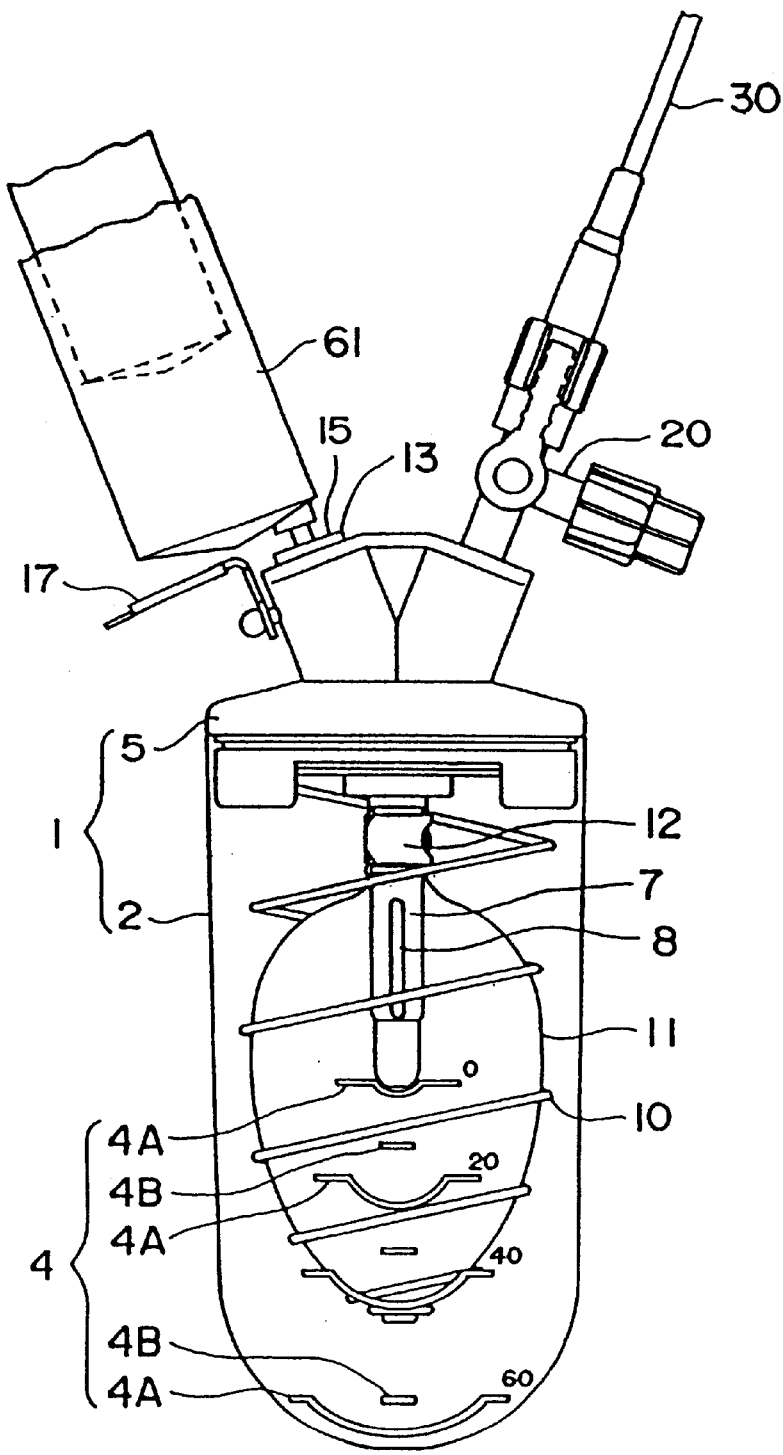
FIG. 10 is an illustration showing a condition in injecting medical fluid into the apparatus of the aforesaid embodiment.

When the medical fluid is received in the rubber elastic film 11, the cap 17 is detached from the valve cylinder 15 of the check valve 13 and a pointed end of a syringe 61 in which the medical fluid is contained is inserted in the valve cylinder 15 of the check valve 13 as shown in FIG. 10. When the medical fluid inside the syringe 61 is pushed out at this state, the medical fluid is received inside the rubber elastic film 11 through the check valve 13 to expand the rubber elastic film 11. The spring 10 is stretched in proportion to the expansion of the rubber elastic film 11, so that the amount of the medical fluid received inside the rubber elastic film 11 can be read by the value of the scale 4 corresponding to the pointed end of the spring 10.

Subsequently, the rubber elastic film 11 abuts an inside of the cylinder body 2 of the protection case 1. Since the cross-section of the protection case 1 is formed in oval configuration as shown in FIG. 10, the contact area of the rubber elastic film 11 with the protection case 1 can be reduced as compared with circular configuration. Further, since the air flow inside the protection case 1 can be ensured, the air inside the cylinder body 2 are discharged to the outside through the water-repellant breathable filter 9A in accordance with the expansion of the rubber elastic film 11. Accordingly, the medical fluid can be accurately delivered little by little, and the attachment position of the air vent 9 is not restricted. After receiving the medical fluid, the valve seat 14 of the check valve 13 is shut when the pointed end of the syringe 61 is pulled out from the check valve 13. Accordingly, the medical fluid inside the rubber elastic film 11 does not leak to the outside.

When the medical fluid is injected into human body, the protection case 1 is accommodated in a breast pocket of patient and the intermediate station 40 is attached to wrist using bands 42 and 43. Accordingly, since the upstream tube 30 runs across the arm from the breast pocket to the wrist and the downstream tube 27 runs parallel to the upstream tube 30, the syringe needle 29 attached to a distal end of the downstream tube 27 can be easily inserted into the arm of the patient. More specifically, the syringe needle 29 can be inserted into the patient's arm while respective tubes stays approximately along the arm without largely bending and twisting them.

When the cock 23 of the three-direction valve 20 is opened in the condition, the medical fluid is sequentially introduced to the human body through the upstream tube 30, the flow rate switching device 40 and the tube 27 at a small flow rate. Incidentally, the small flow rate of the present invention usually refers to around 0.8 ml/hr. However, the flow rate can be optionally determined in accordance with configuration of the deformed opening, length and viscosity of the medical fluid and is not restricted to the above flow rate.

At this time, the medical fluid reaches the intermediate station 40 from the flow path 32A of the tube element 32.

When the medical fluid is discharged from the two flow paths 31A and 32A to the intermediate station 40 at the initial stage and the medical fluid from one channel 31A to the fluid outlet 51, initial air removal can be efficiently conducted since the medical fluid from the other flow path 32A reaches the check valve 54, in other words, since the reservoir 53 and the second communicating channel 55 are filled with the medical fluid thus eliminating air.

When the patient feels pain, the patient himself pushes the pressing member 56 by finger and the like so that the tube (reservoir 53) is pressed. Then, the medical fluid stored inside is pushed out toward the second communicating channel 55 and is injected into human body through the check valve 54 and the downstream tube 27. Accordingly, the predetermined amount of medical fluid can be injected into human body at a stroke as necessary during continuous injection.

Subsequently, when the finger is released from the pressing member 56, the medical fluid is filled inside the tube (the reservoir 53). In accordance therewith, the pressing member 56 returns to original position. At this time, by touching the guide wall 57 by finger etc., whether the fluid is filled in the tube (the reservoir 53) can be checked. Accordingly, confirmation is possible in darkness such as night.

Thus, when all the medical fluid in the rubber elastic film 11 is injected into the human body changing the flow rate as necessary, the medical fluid is filled in the rubber elastic film 11 similarly to the above description and the above-described operation is repeated. Incidentally, in order to remove air inside the rubber elastic film 11 before entering the syringe needle 29 to the human body, the protection case 1 is set upright with the lid body 5 upward and leave it while the cock 23 is made open.

Since the tube 30 having thereinside the elongated thermoplastic-resin-made tube elements 31 and 32 with deformed openings 36A to 36E is used as a flow rate control means instead of conventional short tube having circular opening, the flow rate can be controlled precisely by optionally setting the configuration of the opening and the tube length. When a conventional tube with circular opening is used as a conduit and a dust of a larger size than the inner diameter thereof is contained in the medical fluid or the medical fluid is likely to be coagulated, the medical fluid flow tend to be entirely stopped because the opening is shut. On the other hand, since the tube 30 having predetermined tube elements 31 and 32 having deformed opening configuration is employed, the long side of the deformed opening 36A to 36E is not shut by dust. Accordingly, the blocking of the opening 36A to 36E can be more effectively prevented than the conventional tube having circular opening when the medical fluid contains foreign substance such as dust and solid substance.

Though the tube with the conduit of the conventional tube having circular opening tends to be bent to shut by the weight of a lying patient, the tube elements 31 and 32 having deformed opening according to the present embodiment is tough against bend and is not likely to be shut even when the weight is applied. Therefore, the fluid delivering apparatus without shutting is safer and is significantly effective in a medical field where safety is of importance.

Furthermore, since the conduit function and the flow rate control function are both performed by the tube elements 31 and 32, the structure is simpler than the conventional combination of conduit tube and the flow rate control means.

When the conventional stainless thin tube and glass thin tube is used for performing both the conduit function and the flow rate control function, they are apt to be cracked, broken and difficult to be handled for being too thin. However, since the tube 30 made of thermoplastic resin is used in the present embodiment, deformed opening 36A to 36E having the predetermined configuration is easy to be manufactured, handled easily and both of the conduit function and the minute flow rate control function can be performed.

Incidentally, the scope of the present invention is not limited to the above embodiment and improvement and modification are also included within the scope of the present invention so long as the object of the present invention can be attained.

Though the fluid passage rate of the two flow path 31A and 32A provided in the upstream tube 30 are made identical in the above-described embodiment, the flow paths may have different fluid passage rate. For instance, when the fluid passage rate of the flow path 32A for filling the reservoir 53 is larger than the fluid passage rate of flow path 31A, the time for completing filling process of the reservoir 53 can be shortened.

In the aforesaid embodiment, the plurality of tube elements 31 and 32 is bundled and the outside thereof is unitedly covered by the covering member 35 to make a single tube. However, a thin core member may be set at a predetermined position in forming the tube and resin may be filled to the outside, so that the tube having thereinside a plurality of flow paths can be integrally formed after removing the core member.

The present invention can be applied to medical fluid injecting apparatus for wide range of medical field. The present invention can also be used for injecting medical fluid and nutrients to living body such as animals and fishes.

The present invention can also be used for gradually delivering water, (fluid) nutrients and medical fluid (insecticide) to a plant. For instance, in order to gradually supply the water or the (fluid) nutrients in raising vegetables and flowers, it is only required that the distal end of the tube 30 or a needle attached to the distal end of the tube 30 is buried to the grounds around the vegetables and flowers. In the arrangement, the opening of the tube 30 is not shut even when the tube 30 is treaded on to bend the tube 30, thereby not interrupting the delivery of the fluid. When the medical fluid is injected into trees, it is only required that the protection case 1 is hanged to the trees by an appropriate means and the needle at the distal end of the tube 30 is entered to the trees. In this case, the fluid is not limited to flow out downward from the banged protection case 1 but the medical fluid can be injected to an upper position of the protection case 1.

Further, the present invention can be applied for gradually delivering medical fluids such as antibiotics, (fluid) bait and (fluid) nutrients for water grass to fish aquarium. In this case, the distal end of the tube 30 may be positioned in the aquarium without attaching the needle.

What is claimed is:

1. A fluid supplying apparatus, comprising:

a fluid container for containing fluid;

an upstream tube of which base end is connected to the fluid container for leading the fluid contained in the fluid container;

an intermediate station provided at a distal end of the upstream tube; and a downstream tube connected to the intermediate station for introducing the fluid going through the intermediate station, the upstream tube being formed in a predetermined length and having therein at least two flow paths along a longitudinal direction thereof, the intermediate station including a case provided at the distal end of the upstream tube, the case having a fluid outlet to which the downstream tube is connected, a first communicating channel for intercommunicating the fluid outlet and one of the flow paths of the upstream tube, a reservoir in communication with the other flow path of the upstream tube for storing the fluid introduced through the other flow path, a second communicating channel for intercommunicating the reservoir and the fluid outlet and having a check valve at an intermediate portion thereof, and a discharging means for pushing out the fluid stored in the reservoir to the second communicating channel.

2. The fluid supplying apparatus according to claim 1, wherein the at least two flow paths are made of thermoplastic tube elements of a predetermined length having deformed opening cross section.

3. The fluid supplying apparatus according to claim 1, wherein the upstream tube and the downstream tube are connected on the same side of the intermediate station.

4. The fluid supplying apparatus according to claim 1, wherein the reservoir is made of a balloon for expanding and contracting in accordance with fill and discharge of the fluid, and wherein the discharging means is made of a pressing member insertable into the case and returnable to original position thereof for pressing the balloon when being pressed and returning to the original position in accordance with fill of the fluid into the balloon.

5. The fluid supplying apparatus according to claim 4, wherein a guide wall to be flat with an upper face of the pressing member when the pressing member returns to the original position is provided to at least a part of the surrounding of the case encircling the pressing member.

6. The fluid supplying apparatus according to claim 1, wherein volume of the first communicating channel is defined so that, when the fluid is discharged into the intermediate station from the at least two flow paths of the upstream tube, time for the fluid from one flow path to reach the fluid outlet is longer than time for the fluid from the other flow path reaches the check valve.

* * * * *